(12) United States Patent
Philips et al.

(10) Patent No.: US 8,298,569 B2
(45) Date of Patent: Oct. 30, 2012

(54) OPHTHALMIC EMULSIONS CONTAINING AN IMMUNOSUPPRESSIVE AGENT

(75) Inventors: Betty Philips, Antony (FR); Severine Bague, Marcoussis (FR); Laura Rabinovich-Guilatt, Paris (FR); Gregory Lambert, Chatenay Malabry (FR)

(73) Assignee: Novagali Pharma SA, Evry (FR)

( * ) Notice: Subject to any disclaimer, the term of this patent is extended or adjusted under 35 U.S.C. 154(b) by 1000 days.

(21) Appl. No.: 11/665,066

(22) PCT Filed: Oct. 10, 2005

(86) PCT No.: PCT/EP2005/011649
§ 371 (c)(1),
(2), (4) Date: Apr. 11, 2007

(87) PCT Pub. No.: WO2006/050837
PCT Pub. Date: May 18, 2006

(65) Prior Publication Data
US 2009/0028955 A1    Jan. 29, 2009

Related U.S. Application Data

(63) Continuation-in-part of application No. 10/991,346, filed on Nov. 18, 2004.

(30) Foreign Application Priority Data

Nov. 9, 2004    (EP) ..................................... 04292645

(51) Int. Cl.
*A61K 9/14*    (2006.01)
*A61F 2/00*    (2006.01)
*C07C 231/00*    (2006.01)
(52) U.S. Cl. ........................... 424/427; 424/489; 554/52
(58) Field of Classification Search ........................ None
See application file for complete search history.

(56) References Cited

U.S. PATENT DOCUMENTS

| 4,839,342 | A | | 6/1989 | Kaswan |
| 5,496,811 | A | * | 3/1996 | Aviv et al. ........................ 514/78 |
| 5,698,219 | A | * | 12/1997 | Valdivia et al. ............... 424/450 |
| 6,007,826 | A | | 12/1999 | Benita et al. |
| 6,872,705 | B2 | * | 3/2005 | Lyons ............................ 514/2.3 |
| 2005/0059583 | A1 | * | 3/2005 | Acheampong et al. ......... 514/11 |

FOREIGN PATENT DOCUMENTS

| EP | 0 696 452 | 2/1996 |
| WO | 03/053405 | 7/2003 |
| WO | WO 2005/032577 | 4/2005 |

OTHER PUBLICATIONS

Klang et al., Influence of Emulsion Droplet Surface Charge on Indomethacin Ocular Tissue Distribution, 2000, Pharmaceutical Development and Technology, vol. 5, No. 4, pp. 521-532.*
"The Potential of lipid emulsion for ocular delivery of lipophilic drugs," Tamilvanan et al., European Journal of Pharmaceutics and Biopharmaceutics, Elsevier Science Publishers B.V., vol. 58, No. 2, Jun. 1, 2004, pp. 357-368, XP004526318.
"Cyclosporine Ophthalmic o/w Emulsion: Formulation and Emulsion Characterization," Ding et al., Pharmaceutical Research, vol. 14, No. 11, Nov. 1997, p. S41, XP008005736.
Woo-Jeong Choi et al., "Low toxicity of cationic lipid-based emulsion for gene transfer", Biomaterials, 2004, pp. 5893-5903, vol. 25, Elsevier Ltd.
Gary Ott et al., "A cationic sub-micron emulsion (MF59/DOTAP) is an effective delivery system for DNA vaccines", Jounral of Controlled Release, 2002, pp. 1-5, vol. 79, Elsevier Science B.V.
Satoshi Ogawa et al., "Production and Characterization of O/W Emulsions Containing Cationic Droplets Stabilized by Lecithin-Chitosan Membranes", Journal of Agricultural and Food Chemistry, 2003, pp. 2806-2812, vol. 51, American Chemical Society.

* cited by examiner

*Primary Examiner* — Lezah Roberts
*Assistant Examiner* — Nannette Holloman
(74) *Attorney, Agent, or Firm* — Young & Thompson

(57) ABSTRACT

Ophthalmic oil-in-water emulsions, which comprises colloid particles having an oily core surrounded by an interfacial film, the emulsion comprising an 10 immunosuppressive agent, an oil, preferably at least 50% of which being MCT, and tyloxapol. Use of such an emulsion for the manufacture of medicament for treatment of eye conditions, particularly of dry eye diseases.

9 Claims, 2 Drawing Sheets

OPHTHALMIC EMULSIONS CONTAINING AN IMMUNOSUPPRESSIVE AGENT

FIELD OF THE INVENTION

This invention relates to ophthalmic compositions, preferably ophthalmic emulsions, comprising an immunosuppressive agent as an active ingredient, in a specific vehicle containing oil and preferably tyloxapol, and being suitable for the treatment of eye conditions, particularly of dry eye diseases.

BACKGROUND OF THE INVENTION

Dry eye disease, in the meaning of this invention, relates to any condition relating to ocular dryness and/or tear deficiency, including but not limited to conditions related to a pathological evaporation of fluid from the cornea surface, or conditions related to defective tear film, or more generally any corneal or conjunctive dryness, which can be due to insufficient production of tears, and the conditions resulting therefrom, such as corneal keratitis or corneal epithelium erosion. For example keratoconjunctivis sicca (KCS), atopic keratoconjunctivitis sicca (AKC) and vernal keratoconjunctivitis (VKC) are dry eye diseases.

Cyclosporines are a large class of peptide compounds having various pharmaceutical applications, such as immunosuppressant and anti-inflammatory applications. Cylosporines include cyclosporine A, B, C and D. The most widely investigated cyclosporin is cyclosporin A and cyclosporine A derivatives. Other common immunosuppressive agents are sirolimus or tacrolimus and their derivatives.

Cyclosporine oil-in-water ophthalmic emulsions have been described, and among them the emulsions commercialized by Allergan under the trademark name Restasis® (cyclosporine ophthalmic emulsion 0.05%).

U.S. Pat. No. 4,839,342 describe the use of cyclosporin for the treatment of immune keratoconjunctivis sicca (KCS), and a method of increasing tear production for a tear-deficient eye, in particular directed to a patient suffering from a immune mediated dysfunction of lacrimal glands. The method disclosed in this patent includes administering cyclosporine, preferably cyclosporine A, with a pharmaceutical excipient being olive oil, arachis oil, castor oil or mineral oil.

Shulin Ding and Orest Olejnik have published a poster in the AAPS annual meeting on Nov. 3, 1997; this document relates to castor oil-based oil-in-water emulsions using 0.1 to 0.4% cyclosporine and having a weight ratio cyclosporine/oil of 0.08. This poster discloses that the concentration in cyclosporine A in the oil is optimized at the level of 7.4% w/w which is below the solubility of the cyclosporine in the specific oil vehicle castor oil (10% w/w).

WO2005/032577 describes a method for treating an eye of a human comprising administering an emulsion comprising less than 0.1% cyclosporine and having a weight ratio cyclosporine/castor oil of less than 0.08.

Although this above cited patent application describes further oils, it is not obvious to one skilled in the art that cyclosporine will have the same behaviour in any oily vehicle, because it does not have the same solubility in all oils, and the bioavailability of the cyclosporine in one oily vehicle does not give information on its bioavailability in another oily vehicle.

An emulsion is a system consisting of two immiscible liquid phases, one of which, in fine droplets, is dispersed throughout the other, the system being stabilized by a third component, the emulsifying agent. Emulsions are inherently unstable, and emulsifiers are essential for both their initial formation and long-term stability.

Due to their small droplet size, submicronic or nano-emulsions may appear transparent, and Brownian motion prevents sedimentation or creaming, hence offering increased stability.

The instability of an emulsion will appear as phase separation due to creaming (density differences), Ostwald ripening (disproportionation) flocculation (aggregation through interparticle collision), and coalescence (fusion of separate droplets). An important distinction is that flocculation is often reversible while coalescence is not. The process of droplet coalescence is the normal way in which an emulsion coarsens with time, i.e. the mean particle size of the droplet increases upon storage.

Presence of larger aggregates promotes faster creaming and thus facilitates coalescence. This is especially true for polydisperse systems where different creaming rates produce enhanced droplet encounter rates. As a consequence, the droplet size distribution of an emulsion governs emulsion properties such as long-term stability.

Therefore, a monomodal droplet population has the benefits of increased stability besides of the drug content uniformity which is essential in pharmaceutical applications for the administration of a correct drug dose.

Even though the prior art formulations, such as Restasis®, are currently useful to treat conditions for which few treatment are available, it is known that the bioavailability of the prior art formulations is not optimal, and one of the known drawbacks of Restasis®, for example, is that it may take several weeks to take full effect. In addition, castor oil-based cyclosporine emulsion such as Restasis® presents a bimodal droplet population (Ding, abstract AAPS 1997). Such formulation is expected to have decreased shelf life as a result of the coalescence of the oil droplets.

There is therefore still a need for alternative solutions for treating dry eye conditions, with emulsions having at least the same physico-chemical stability properties and improved bioavailability of the drug. In the sense of this invention, bioavailability means the percentage of drug that can be detected in the target ocular tissue after its administration. Detection of the drug can be accomplished pharmacodynamically (quantification of a biological response to the cyclosporine) or pharmacokinetically (quantification of actual drug concentration).

Moreover, patients suffering from dry eye diseases have very sensitive eyes, and it is an objective of this invention to provide a composition providing comfort as well as therapy.

SUMMARY OF THE INVENTION

It is a goal of this invention to provide ophthalmic emulsions having these properties. Accordingly, the emulsions of this invention comprise a combination of ingredients, allowing them to respond to both requirements of stability and bioavailability.

Thus, this invention relates to ophthalmic emulsions which comprise colloid particles having an oily core surrounded by an interfacial film, said emulsion comprising at least one immunosuppressive agent, preferably selected from the group consisting of cyclosporine, sirolimus, tacrolimus, in a vehicle comprising an oil and tyloxapol.

DETAILED DESCRIPTION OF THE INVENTION

Figure 1:
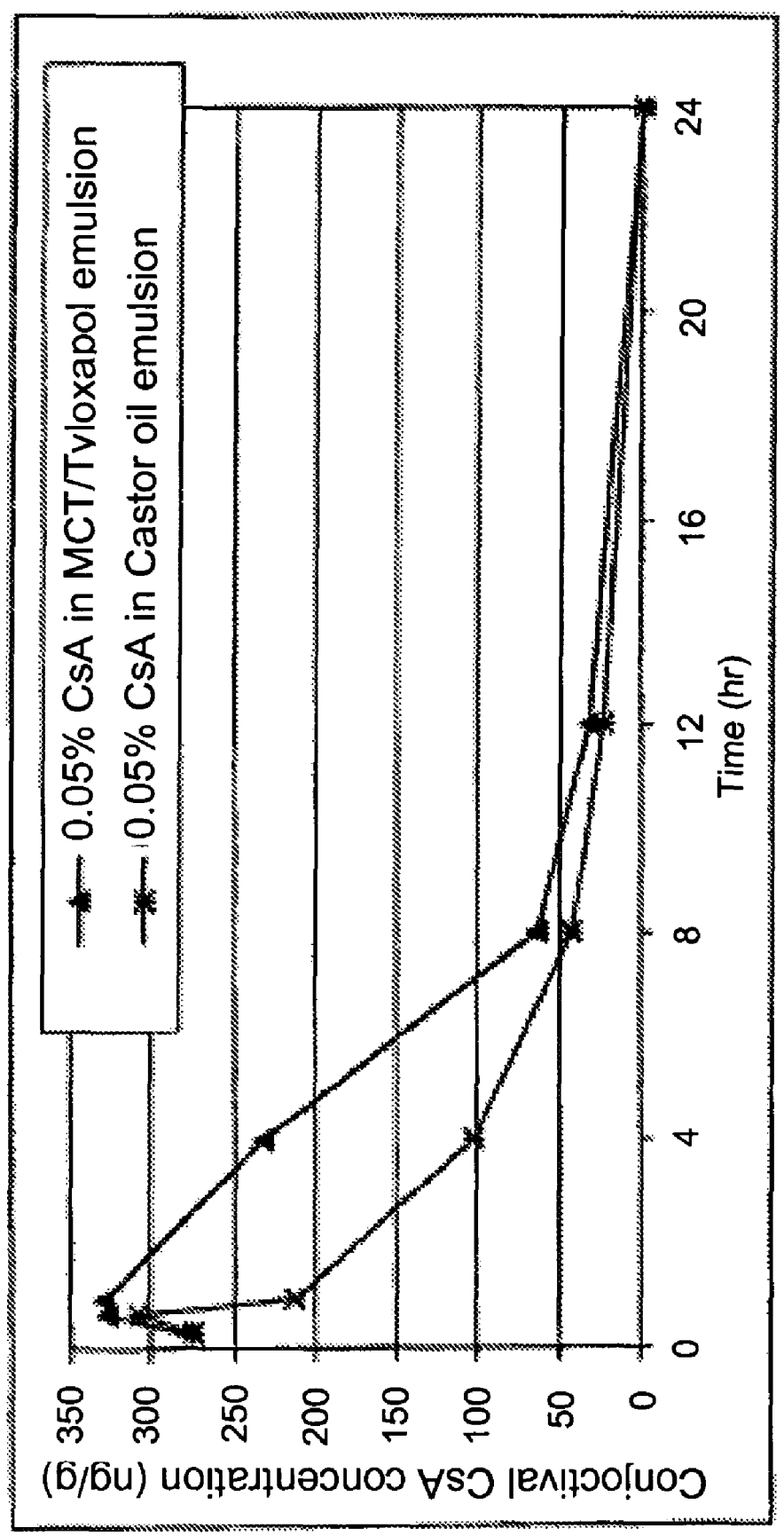
FIG. 1 depicts a graphical representation of the results of Example 7, which compares the tissue concentration of CsA (Cyclosporin A) resulting from the emulsions according to the present invention to the CsA concentration resulting from castor oil-based marketed emulsions Restasis®.
Figure 2:
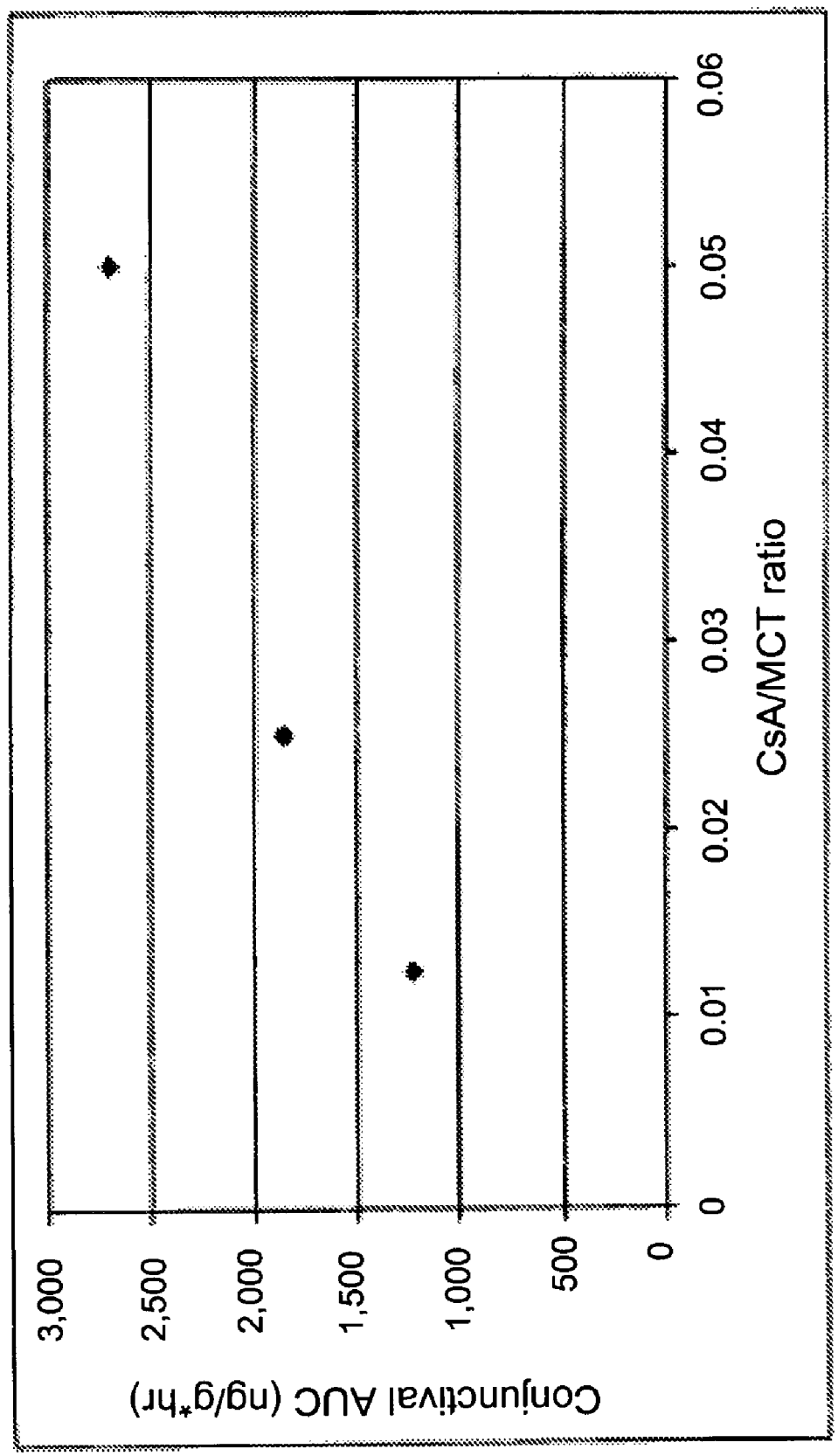
FIG. 2 depicts a graphical representation of the results from Example 8, which shows linear correlation between CsA/oil ratio and conjunctival concentration resulting from the emulsions according to the present invention.

It has been surprisingly found by the inventors that the use of MCT, a vegetal oil selected among all, provides unexpected stability and bioavailability to cyclosporine-containing ophthalmic emulsions. MCT has also been found by the inventors to better solubilize cyclosporine, which may play a role in the observed improved bioavailability of cyclosporine in the emulsions of the invention (Examples 1-6). According to an embodiment of the invention, the amount of MCT is at least 50% in weight of MCT by weight of the total oil content of the emulsion. According to a preferred embodiment, the oil content of the emulsion is 100% MCT. Advantageously, the amount of MCT is from 0.5 to 4%, preferably 0.9 to 3%, more preferably to 2% w/w of the emulsion.

According to a preferred embodiment of the invention the amount of tyloxapol is less than 1%, preferably comprised between 0.01 to 0.6% by weight of the total weight of the emulsion.

Even more surprisingly, the inventors have found that MCT, when combined with tyloxapol, provide even better results in terms of bioavailability of an immunosuppressive agent (Example 7). The inventors have demonstrated a synergistic effect of tyloxapol and MCT in an ophthalmic emulsion of the invention containing an immunosuppressive agent, especially cyclosporine, sirolimus or tacrolimus.

Finally, WO2005/032577 describes 1.25% castor-oil based emulsions for which increasing the amount of cyclosporine from 0.05% to 0.1% (and therefore the CsA/oil ratio from 0.04 to 0.08) does not improve the overall efficacy in treating dry eye disease. Contrary to this teaching, the Inventors have unexpectedly found that, when increasing the amount of immunosuppressive agent in the emulsions of the invention, an increasing amount of drug is transferred into the ocular target (see example 8); this means that the emulsions of the invention are not limited to a specific ratio of immunosuppressive agent/oil. Thus, the emulsions of the invention make it possible to increase the therapeutic amounts of drugs to be delivered of the target site, thus increasing the therapeutic values of the used immunosuppressive agent.

According to an embodiment of the invention, the emulsion may further include any other suitable oily components, especially one or more oils selected from the group consisting of, olive, soy, corn, mineral, cottonseed, safflower, sesame. According to a preferred embodiment of the invention, the emulsions are free of castor oil.

In a first embodiment of the invention, the emulsion is anionic. According to a preferred embodiment, the emulsion of the invention includes one or more components selected from the group consisting of phospholipids, cholic acid and its derivatives, metal carboxymethylcelluloses, metal carboxymethylhydroxyethylcelluloses, metal carboxymethylstarchs metal, carboxy methylhydroxyethylstarchs hydrolyzed polyacrylamides and polyacrylonitriles heparin gucoaminoglycans hyaluronic acid chondroitin sulphate, dermatan sulphate, peptides and polypeptides alginic acid, metal alginates homopolymers and copolymers of one or more of: acrylic and methacrylic acids metal acrylates and methacrylates vinylsulfonic acid, metal vinylsulfonate, amino acids, such as aspartic acid, glutamic acid and the like metal salts of amino acids p-styrenesulfonic acid metal p-styrenesulfonate, 2-methacryloyloxyethylsulfonic acids, metal 2-methacryloyloxethylsulfonates, 3-methacryloyloxy-2-hydroxypropylsulonic acids metal 3-methacryloyloxy-2-hydroxypropylsulfonates, 2-acrylamido-2-methylpropanesulfonic acids metal 2-acrylamido-2-methylpropanesulfonates allylsulfonic acid metal allylsulfonate and the like.

In a second embodiment of the invention, the emulsion is cationic. In this embodiment, it is preferred that the concentration of the cationic agent is comprised between 0.001 and 0.1% w/w, preferably between 0.002 and 0.05% w/w and still more preferably between 0.003 and 0.03% w/w. This second embodiment is particularly preferred, because it has been found that the cationic charge of the emulsion improves the bioavailability of the cyclosporine contained in the emulsion. Advantageously, the cationic cyclosporine-containing ophthalmic emulsion of the invention is an oil-in-water type emulsion, which comprises colloid particles having an oily core surrounded by an interfacial film, said emulsion comprising at least one cationic agent, at least one non ionic tensioactive, said emulsion having a positive zeta potential. According to a preferred embodiment, the cationic ophthalmic emulsion of the invention meets the zeta potential stability Test A requirements as described below:

Test A consists in measuring the stability of the emulsion zeta potential under thermal stress conditions.

Zeta potential of the emulsion is measured at $T=0$, i.e. as soon as the emulsion has been prepared, the obtained value being named $Z_0$. Glass vials (Type I) of 10 ml effective capacity containing between 5-10 ml of emulsion and sealed under nitrogen atmosphere (without bubbling) are stored at 80° C.

Then at $T=7$ days the zeta potential $Z_{7days}$ is measured.
Then at $T=15$ days the zeta potential $Z_{15days}$ is measured.
The value $\delta A = Z_{7h} - Z_0$ or $Z_{15h} - Z_0$ is then calculated.

For each measurement of the zeta potential, it is operated as follows:

The zeta potential of the emulsion droplet surface is determined by electrophoretic mobility in an apparatus such as a Malvern Zetasizer 2000 (Malvern Instruments, UK) equipped with suitable software and calibrated with the supplied standard.

The emulsion is diluted in double distilled water if needed in order to obtain the scattering intensity allowing optimal particle detection. The sample count rate should be between 100 to 1000 KCps, in homodyne detection (if heterodyne detection is used, the contribution of the reference beam should be deduced). Three consecutive measurements are performed at 25° C. using a constant cell drive of 150 mV. The electrophoretic mobility is converted into zeta potential values through the Smoluchowsky equation, using the dielectric constants and viscosity of water. The measured value corresponds to the average of the 3 obtained values.

It is considered that the emulsion meets zeta potential stability Test A if $\delta A$ is less than the standard error of measurements, preferably less than 10 mV, and even more preferably less than 5 mV.

In a preferred embodiment of the invention, the emulsion of the invention contains cyclosporine A. Advantageously, the emulsion of the invention contains from 0.01 to 0.4% w/w, preferably 0.05 to 0.3% of immunosuppressive agent, preferably cyclosporine, more preferably cyclosporine A. According to another embodiment of the invention, the emulsion comprises an amount of tacrolimus of 0.01 to 0.3% w/w, preferably 0.05 to 0.2% w/w of the emulsion. According to still another embodiment of the invention, the emulsion comprises an amount of sirolimus of 0.01 to 0.3% w/w, preferably 0.05 to 0.2% w/w of the emulsion.

In another preferred embodiment of the invention, the weight ratio of immunosuppressive agent to oil is from 0.0125 to 0.1. In a particular embodiment of the invention, the emulsion of the weight ratio of immunosuppressive agent to oil is from 0.083 to 0.1. In another particular embodiment of the invention, the emulsion of the weight ratio of immunosuppressive agent to oil is from 0.0125 to 0.05. Advantageously, the emulsion of the invention is submicronic, and in a very preferred embodiment, monomodal submicronic, which means that the colloid particles of the invention are very homogeneous in their size equal or less than 1 μm, in that they have a droplet size polydispersity index close to 0.2, generally between 0.1 and 0.15. The calculation of the polydispersity index is defined in the ISO standard document 13321:1996 E.

Preferably, colloid particles of the emulsion of the invention have an average particle size of equal or less than 1 μm, advantageously equal or less than 300 nm, more advantageously in the range of 100 to 250 nm.

According to a preferred embodiment of the invention the emulsions of the invention are cationic submicronic emulsions, and do not contain any substances capable of generating a sufficient amount of negative charge for affecting the positive zeta potential of the emulsion. In this embodiment, advantageously, the emulsion does not contain phospholipids.

The invention also relates to a process of preparation of the emulsions containing at least one immunosuppressive agent, preferably chosen in the group consisting of cyclosporine, preferably cyclosporine A, sirolimus or tacrolimus and MCT and tyloxapol according to the invention, comprising one step of shear mixing followed by a high pressure homogenization.

The best mode of making and using the present invention are described in the following examples. These examples are given only to provide direction and guidance in how to make and use the invention, and are not intended to limit the scope of the invention in any way.

EXAMPLES

In the following examples, the following abbreviations are used:
MCT: Medium chain triglycerides (Société des Oléagineux, France)
BAK: Benzalkonium chloride
CsA: Cyclosporin A
Cremophor: Cremophor EL (BASF, Germany)
Lipoid E80 (Lipoid GMBH, Germany)
Lutrol: Lutrol F68 (BASF, Germany)
Pemulen TR-2 (Noveon, US)
Phospholipon 90G (Natterman, Germany)

Example 1

Preparation of the Emulsions of this Invention

The oily phase components are successively weighed and then stirred under a slight heating until a limpid and slightly viscous phase is obtained. Aqueous phase components are successively weighed and then magnetically stirred under a slight heating until a transparent, limpid and fluid phase is obtained. Both phases are heated and the coarse emulsion is formed by rapid addition of the aqueous phase in the oily phase and then rapidly heated to 75° C. The emulsion is white and slightly transparent. The emulsion droplet size is then decreased by high shear mixing by using for example a POLYTRON PT 6100, followed by its cooling down.

Final emulsion is obtained by high pressure homogenization in suitable equipment such as microfluidizer (C5, Avestin) using several continuous cycles. Final emulsion is milky and very fluid. The emulsion temperature is then decreased to 25° C., its pH was measured and then adjusted to 6.0, 7.0, 8.0 using a 0.1 M HCl or 0.1 M NaOH solution. Sterilization can be done by autoclave 20 minutes at 121° C. or by filtration through a 0.22 um filter.

Example 2

Characterization of the Emulsions of this Invention

The mean particle size of the emulsions droplets is determined by quasi-elastic light scattering after dilution in water using for example a High Performance Particle Sizer (Malvern Instruments, UK). This instrumentation is also used to determine the polydispersity index. The electrophoretic mobility is measured at 25° C. in an appropriate apparatus such as Malvern Zetasizer 2000 (Malvern Instruments, UK) following a 1:200 dilution in double distilled water and converted into zeta potential through the Smoluchowski equation.

CsA in the emulsion is determined by a validated HPLC-UV method.

Example 3

Compositions of this Invention Containing CsA/Oil/Tyloxapol

| Ingredient | EM047 | EM048 | EM049 | EM050 | EM051 | EM052 | EM053 |
|---|---|---|---|---|---|---|---|
| CsA | 0.025 | 0.025 | 0.05 | 0.05 | 0.2 | 0.2 | 0.1 |
| MCT | 0.75 | 2 | 1 | 2 | 2 | 4 | 2 |
| BAK | 0.02 | 0.02 | 0.02 | 0.02 | 0.02 | 0.02 | 0.02 |
| Tyloxapol | 0.12 | 0.3 | 0.16 | 0.3 | 0.3 | 0.3 | 0.3 |
| Poloxamer | 0.1 | 0.1 | 0.1 | 0.1 | 0.1 | 0.1 | 0.1 |
| Vitamin E | 0.01 | 0.01 | 0.01 | 0.01 | 0.01 | 0.01 | 0.01 |
| Glycerin | 2.25 | 2.25 | 2.25 | 2.25 | 2.25 | 2.25 | 2.25 |
| Purified water | qs | qs | qs | qs | qs | qs | qs |

Example 4

Stability of Compositions of this Invention

Methods:

Stability of the emulsions is assessed by measuring physicochemical parameters such oil droplet size, zeta potential and CsA content after sterilization by autoclave or filtration and during an accelerated stability test at 80° C.

Results:

| Emulsion | | EM047 | EM048 | EM049 | EM050 | EM051 | EM052 | EM053 |
|---|---|---|---|---|---|---|---|---|
| Emulsion globule size (nm) | T0 | 172 | 182 | 151 | 211 | 188 | 170 | 204 |
| | T7 | 188 | 193 | 173 | 212 | 195 | 201 | 211 |
| | T14 | 194 | 200 | 177 | 221 | 206 | 195 | 226 |
| Polydispersity index | T0 | 0.155 | 0.144 | 0.148 | 0.116 | 0.078 | 0.138 | 0.108 |
| Zeta potential (mV) | T0 | 20.9 | 19.6 | 25.0 | 17.9 | 20.1 | 28.4 | 23.5 |
| | T7 | 18.9 | 19.6 | 24.7 | 20.3 | 21.9 | 24.5 | 23.2 |
| | T14 | 16.9 | 19.4 | 19.2 | 18.5 | 19.0 | 23.0 | ND |
| CsA (% of initial content) | T0 | 100.0% | 100.0% | 100.0% | 100.0% | 100.0% | 100.0% | 100.0% |
| | T7 | 96.4% | 97.5% | 97.8% | 95.8% | 92.8% | 96.0% | 97.4% |
| | T14 | 94.6% | 96.4% | 96.0% | 94.2% | 88.2% | 96.6% | 94.8% |

ND: Not determined

Conclusions:

MCT/Tyloxapol-based emulsions of CsA produced by the process of the invention including a shear mixing step followed by a high pressure homogenisation step are stable following preparation and for at least two weeks at 80° C.

Example 5

Comparative Example—Compositions Containing CsA/Castor Oil

| EMCIC007 | | EMCIC003 | | Restasis ® | |
|---|---|---|---|---|---|
| Ingredient | % w/w | Ingredient | % w/w | Ingredient | % w/w |
| CsA | 0.2 | CsA | 0.2 | CsA | 0.05 |
| Castor oil | 2.5 | Castor oil | 2.5 | Castor oil | 1.25 |
| Oleylamine | 0.12 | Stearylamine | 0.12 | — | — |
| Phospholipon 90G | 0.5 | Lipoid E80 | 0.5 | Polysorbate 80 | 1 |
| Lutrol F68 | 0.42 | Lutrol F68 | 0.42 | Pemulen TR-2 | 0.05 |
| Glycerin | 2.25 | Glycerin | 2.25 | Glycerin | 2.2 |
| Purified water | qs | Purified water | qs | Purified water | qs |

Example 6

Stability of Emulsions Containing CsA/Castor Oil

Methods:

Similar to Example 1-4

Results:

| Emulsion | | EMCIC003 | Restasis ® | EMCIC007 |
|---|---|---|---|---|
| Emulsion globule size (nm) | T0 | Broken emulsion | 279 | Broken emulsion |
| | T7 | ND | 514 (56%) and 2467 (43%) | ND |
| | T14 | ND | Broken emulsion | ND |
| Zeta potential (mV) | T0 | ND | −43.7 | ND |
| | T7 | ND | −41.6 | ND |
| | T14 | ND | ND | ND |
| CsA (% of initial content) | T0 | ND | 100.0% | ND |
| | T7 | ND | 55.3% | ND |
| | T14 | ND | ND | ND |

ND: Not determined.
Percentages indicate the relative populations as measured by scattered light.

Conclusions:

Castor oil-emulsions of CsA produced by homogenisation techniques as described above are not stable following preparation or after one week at 80° C.

Example 7

Efficacy of Emulsions of this Invention as Evaluated by their Pharmacokinetic Parameters Methods:

Ninety-six (96) pigmented rabbits from the HYRNZ104 strain were randomly divided into two (2) treatment groups of forty eight (48) animals, each group being sub-divided into eight (8) subgroups of six (6) animals corresponding to eight (8) time-points (0.33, 0.66, 1, 2, 4, 8, 12 and 24 hrs). The animals received a single instillation into right eyes of the above described EM050 or Restasis® (Allergan, US). At the corresponding time-points, animals were euthanized and the conjunctiva was sampled. Content of CsA was determined by HPLC-MS.

Conclusions:

The emulsions described in this invention show tissue concentrations at least as good as the castor oil-based marketed emulsion Restasis®.

Example 8

Impact of the CsA/Oil Ratio in the Emulsions of this Invention on their Efficacy as Evaluated by their Pharmacokinetic Parameters Methods:

One hundred and forty-four (144) pigmented rabbits from the HYRNZ104 strain were randomly divided into three (3) treatment 20 groups of forty eight (48) animals, each group being sub-divided into eight (8) subgroups of six (6) animals corresponding to eight (8) time-points (0.33, 0.66, 1, 2, 4, 8, 12 and 24 hrs). The animals received a single instillation into right eyes of the above described EM048, EM050 or EM053 (0.025, 0.05 and 0.1% w/w CsA in 2% MCT emulsions). At the corresponding time-points, animals were euthanized and the conjunctiva was sampled. Content of CsA was determined by HPLC-MS. The area under the curve (AUC) indicating the animal exposure to the compound was calculated using the trapezoidal rule.

Conclusions:

The emulsions described in this invention show a linear correlation between the CsA/oil ratio and the conjunctival concentration. As the clinical efficacy is correlated to the CsA concentration, it can be assumed that this particular vehicle will provide increasing therapeutic value for rising amounts of CsA Example 9

Ocular Tolerance of the Emulsions of this Invention

The aim of this study was to determine the ocular tolerance of the emulsions of this invention (EM048, EM050 and EM053; see composition in previous examples) after multiples daily ocular topical administrations for 28 consecutive days into the right eye of albino rabbits.

Methods:

Ten (10) New Zealand White albino rabbits per group (5 males and 5 females) were involved in this study. Treatments (50 □l ocular topical administrations) were given four times a day for 28 consecutive days. General tolerance (body weight, food and water consumptions, general aspect, clinical signs, hematology and blood biochemistry), ocular tolerance (observations with an ophthalmoscope, slit lamp examinations and ocular histology) and necropsy (gross macroscopic examination, main organ weights) were investigated. A statistical analysis (MANOVA LSD test) was also performed on body and organ weights, on food and water consumption data, and on haematological and biochemical parameters Results:

General behaviour, food consumption and water consumption, body weight, organ weights were unaffected by treatments. There were no remarkable observations at necropsy due to treatment. Ophthalmologic observations and microscopic examinations of the eyes and adnexa revealed no adverse effects. Ocular reactions were confined to slight conjunctival redness that were observed in all animals in the study and are commonly observed in rabbits after multiple instillations of ophthalmic products Conclusions:

The emulsions described in this invention are well tolerated following chronic topical administration.

The invention claimed is:

1. An ophthalmic oil-in-water emulsion, which comprises colloid particles having an oily core surrounded by an interfacial film, said emulsion comprising:

0.05 to 0.3% cyclosporine in weight to the total weight (w/w) of the emulsion,
0.5 to 4% w/w medium-chain triglycerides,
0.02% w/w benzalkonium chloride, and
surfactants, wherein the surfactants consist of a mixture of tyloxapol and poloxamer, wherein the tyloxapol is present in an amount of 0.3% w/w and the poloxamer is present in an amount of 0.1% w/w, and wherein said emulsion is cationic, wherein said emulsion meets zeta potential stability under thermal stress conditions as determined by Test A:

measuring zeta potential, in mV, of said emulsion at the time of preparation is $Z_0$, sealing 5-10 ml of said emulsion in 10 ml Type I glass vials under nitrogen atmosphere without bubbling, storing said sealed vials at 80° C. for 7 days, measuring zeta potential, in mV, of said emulsion at 7 days, $Z_{7days}$, determining the difference between $Z_{7days}-Z_0$, $\delta A$, the emulsion meeting the zeta potential stability under thermal stress conditions according to Test A for a $\delta A$ less than the 10 mV standard error of zeta potential measurement, wherein said emulsion does not comprise phospholipids, and wherein said emulsion does not comprise substances capable of generating a negative charge.

2. The ophthalmic oil-in-water emulsion according to claim 1, which can be administered topically.

3. The ophthalmic oil-in-water emulsion according to claim 1, wherein said emulsion comprises 2% w/w of the medium chain triglycerides compared to the total weight of the emulsion.

4. The ophthalmic oil-in-water emulsion according to claim 1 wherein the cyclosporine is or includes cyclosporine A.

5. The ophthalmic oil-in-water emulsion according to claim 1, further including one or more oils selected from the group consisting of olive, soy, corn, mineral, cottonseed, safflower and sesame.

6. The ophthalmic oil-in-water emulsion according to claim 1 wherein said colloid particles of the emulsion of the invention have an average particle size of equal or less than 1 µm, and its size population distribution is monomodal.

7. The ophthalmic oil-in-water emulsion according to claim 1 wherein said colloid particles of the emulsion of the invention have an average particle size of equal or less than 1 µm.

8. A method for treating a dry eye disease comprising administering an effective amount to a subject in need thereof, the ophthalmic oil-in-water emulsion according to claim 1.

9. The method according to claim 8, wherein the dry eye disease is selected from the group consisting of keratoconjunctivis sicca, atopic keratoconjunctivitis sicca and vernal keratoconjunctivitis.

* * * * *